US008324345B2

(12) United States Patent
Miyakawa et al.

(10) Patent No.: US 8,324,345 B2
(45) Date of Patent: Dec. 4, 2012

(54) HLA-BINDING PEPTIDE, PRECURSOR THEREOF, DNA FRAGMENT AND RECOMBINANT VECTOR ENCODING THE SAME

(75) Inventors: Tomoya Miyakawa, Minato-ku (JP); Keiko Udaka, Nankoku (JP)

(73) Assignees: NEC Corporation, Tokyo (JP); Kochi University, Kochi (JP)

( * ) Notice: Subject to any disclaimer, the term of this patent is extended or adjusted under 35 U.S.C. 154(b) by 497 days.

(21) Appl. No.: 12/444,988

(22) PCT Filed: Oct. 3, 2007

(86) PCT No.: PCT/JP2007/069348
§ 371 (c)(1),
(2), (4) Date: Apr. 9, 2009

(87) PCT Pub. No.: WO2008/044567
PCT Pub. Date: Apr. 17, 2008

(65) Prior Publication Data
US 2010/0144025 A1 Jun. 10, 2010

(30) Foreign Application Priority Data
Oct. 12, 2006 (JP) ................. 2006-279232
Jul. 20, 2007 (JP) ................. 2007-189047

(51) Int. Cl.
*A61K 39/12* (2006.01)
*C07K 7/06* (2006.01)
(52) U.S. Cl. ................ 530/327; 424/186.1; 530/328
(58) Field of Classification Search .................. None
See application file for complete search history.

(56) References Cited

U.S. PATENT DOCUMENTS

| 5,824,506 A | 10/1998 | Chan et al. |
| 6,037,135 A | 3/2000 | Kubo et al. |
| 2005/0048472 A1* | 3/2005 | Romette et al. ........... 435/5 |
| 2005/0074423 A1* | 4/2005 | Durand et al. .......... 424/70.14 |

FOREIGN PATENT DOCUMENTS

| JP | 05-336960 A | 12/1993 |
| JP | 08-500106 A | 1/1996 |
| JP | 08-504168 A | 5/1996 |
| JP | 08-151396 A | 6/1996 |
| JP | 08-507080 A | 7/1996 |
| JP | 08-507525 A | 8/1996 |
| JP | 10-501791 A | 2/1998 |
| JP | 10-298198 A | 11/1998 |
| JP | 11-316754 A | 11/1999 |
| JP | 11-318455 A | 11/1999 |
| JP | 2000-116383 A | 4/2000 |
| JP | 2001-504799 A | 4/2001 |
| JP | 2004-099509 A | 4/2004 |
| JP | 2004-154069 A | 6/2004 |
| JP | 2006-008638 A | 1/2006 |
| WO | 93/17699 A1 | 9/1993 |
| WO | 94/03205 A1 | 2/1994 |
| WO | 94/19011 A1 | 9/1994 |
| WO | 94/20127 A1 | 9/1994 |
| WO | 95/26979 A1 | 10/1995 |
| WO | 97/33602 A1 | 9/1997 |
| WO | 99/29715 A1 | 6/1999 |

OTHER PUBLICATIONS

Simmons et al. Early T-Cell Responses to Degue Virus Epitopes . . . Journal of Virology. May 2005, vol. 79, No. 9, pp. 5665-5675.*
Susan J. Gagnon, et al., "Identification of Two Epitopes on the Dengue 4 Virus Capsid Protein Recognized by a Serotype-Specific and a Panel of Serotype-Cross-Reactive Human CD4+ Cytotoxic T-Lymphocyte Clones," Journal of Virology, Jan. 1996, pp. 141-147, vol. 70, No. 1.
Keiko Udaka, et al., "An automated prediction of MHC class I-binding peptides based on positional scanning with peptide libraries," Immunogenetics, 2000, pp. 816-828, vol. 51.
Keiko Udaka, et al., "Tolerance to Amino Acid Variations in Peptides Binding to the Major Histocompatibility Complex Class I Protein H-2K$^b$," The Journal of Biological Chemistry, Oct. 13, 1995, pp. 24130-24134, vol. 270, No. 41.
Keiko Udaka, et al., "Decrypting the Structure of Major Histocompatibility Complex Class I-Restricted Cytotoxic T Lymphocyte Epitopes with Complex Peptide Libraries," J. Exp. Med., Jun. 1995, pp. 2097-2108, vol. 181.
Keiko Udaka, et al., "Self-MHC-Restricted Peptides Recognized by an Alloreactive T Lymphocyte Clone," The Journal of Immunology, 1996, pp. 670-678, vol. 157.
H. Bashyam, "Dengue Virus-Reactive CD8$^+$ T Cells Display Quantitative and Qualitative Differences in Their Response to Variant Epitopes of Heterologous Viral Serotypes" Journal of Immunology, vol. 176, No. 5, Mar. 2006, pp. 2817-2824.
Y. Becker, "Computer Simulations to Predict the Availability of Peptides with Known HLA Class I Motifs Generated by Proteolysis of Dengue Fever Virus (DFV) Type 1 Structural and Nonstructural Proteins in Infected Cells", Virus Genes, Kluwer Academic Publishers, vol. 10, No. 3, Oct. 1, 1995, pp. 195-203.
H. Loke, "Strong HLA Class I-Restricted T Cell Responses in Dengue Hemorrhagic Fever: A Double-Edged Sword?", Journal of Infectious Diseases, vol. 184, No. 11, Dec. 1, 2001, pp. 1369-1373.
J. Mongkolsapaya, "T Cell Responses in Dengue Hemorrhagic Fever: Are Cross-Reactive T Cells Suboptimal?", Journal of Immunology, vol. 176, No. 6, Mar. 15, 2006, pp. 3821-3829.

(Continued)

*Primary Examiner* — Jeffrey E Russel
(74) *Attorney, Agent, or Firm* — Sughrue Mion, PLLC

(57) ABSTRACT

There is provided an HLA-binding peptide being excellent in binding affinity to an HLA-A type molecule. An HLA-binding peptide capable of binding to an HLA-A type molecule, including one or more amino acid sequences selected from the group consisting of SEQ ID NOs: 1 to 50, and being composed of 8 or more and 11 or less amino acid residues, is provided. All of the amino acid sequences are the amino acid sequences that are predicted to be capable of binding to an HLA-A molecule by using a prediction program utilizing an active learning method shown in FIG. 1.

7 Claims, 1 Drawing Sheet

OTHER PUBLICATIONS

G. Zhang, "MULTIPRED: A computational system for prediction of promiscuous HLA binding peptides," Nucleic Acids Research, Oxford University, vol. 33, Jan. 1 2005, pp. W172-W179.

I. Kurane, "Definition of an HLA-DPw2-restricted epitope on NS3, recognized by a dengue virus serotype cross-reactive human CD4+ CD8− cytotoxic T-cell clone," Journal of Virology, vol. 67, No. 10, Oct. 1993, pp. 6285-6288.

A. Hughes, "Evolutionary change of predicted cytotoxic T cell epitopes of dengue virus," Infection, Genetics and Evolution; Journal of Molecular Epidemiology and Evolutionary Genetics in Infectious Diseases, vol. 1 No. 2, Dec. 2001, pp. 123-130.

M. Larsen, "An integrative approach to CTL epitope prediction: A combined algorithm integrating MHC class I binding, TAP transport efficiency, and proteasomal cleavage predictions," European Journal of Immunology, vol. 35, No. 8, Aug. 2005, pp. 2295-2303.

Japanese Office Action issued Sep. 14, 2012, in counterpart Japanese Patent Application No. 2008-538674.

Su, M. et al., "Dengue virus type 2 strain Taiwan-1008DHF polyprotein gene, complete cds", GenBank Accession No. AY776328, The National Center for Biotechnology, Dec. 31, 2005, retrieved from http://www.ncbi.nlm.nih.gov/nuccore/AY776328.1?report=girevhist>.

* cited by examiner

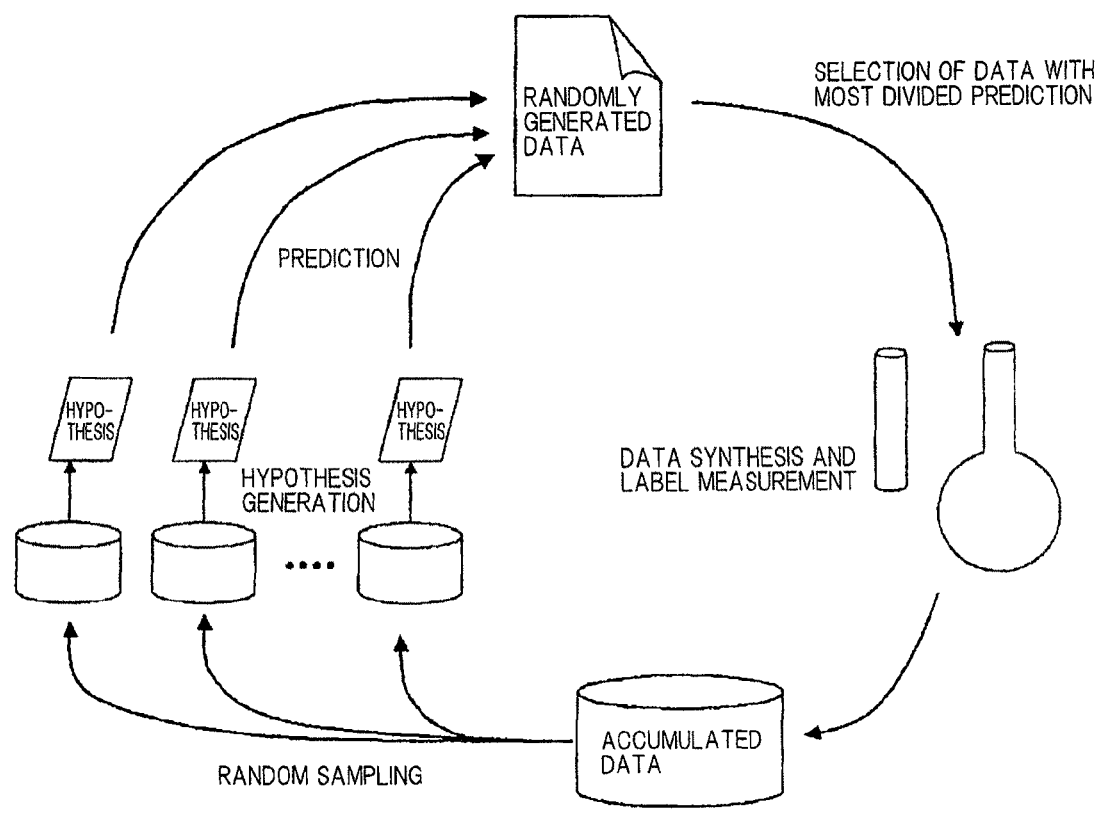

SEQUENCE LISTING

<160> NUMBER OF SEQ ID NOS: 51

<210> SEQ ID NO 1
<211> LENGTH: 9
<212> TYPE: PRT
<213> ORGANISM: Homo sapiens

<400> SEQUENCE: 1

Trp Tyr Ala Gln Ile Gln Pro His Trp
1               5

<210> SEQ ID NO 2
<211> LENGTH: 9
<212> TYPE: PRT
<213> ORGANISM: Homo sapiens

<400> SEQUENCE: 2

Ala Phe Ser Gly Val Ser Trp Thr Met
1               5

<210> SEQ ID NO 3
<211> LENGTH: 9
<212> TYPE: PRT
<213> ORGANISM: Homo sapiens

<400> SEQUENCE: 3

Ile Leu Ile Gly Val Val Ile Thr Trp
1               5

<210> SEQ ID NO 4
<211> LENGTH: 9
<212> TYPE: PRT
<213> ORGANISM: Homo sapiens

<400> SEQUENCE: 4

Met Met Ile Pro Thr Val Val Ala Phe
1               5

<210> SEQ ID NO 5
<211> LENGTH: 9
<212> TYPE: PRT
<213> ORGANISM: Homo sapiens

<400> SEQUENCE: 5

Pro Phe Pro Gln Ser Asn Ala Pro Ile
1               5

<210> SEQ ID NO 6
<211> LENGTH: 9
<212> TYPE: PRT
<213> ORGANISM: Homo sapiens

<400> SEQUENCE: 6

Leu His Lys Leu Gly Tyr Ile Leu Arg
1               5

<210> SEQ ID NO 7
<211> LENGTH: 9

```
<212> TYPE: PRT
<213> ORGANISM: Homo sapiens

<400> SEQUENCE: 7

His Trp Pro Lys Ser His Thr Leu Trp
1               5

<210> SEQ ID NO 8
<211> LENGTH: 9
<212> TYPE: PRT
<213> ORGANISM: Homo sapiens

<400> SEQUENCE: 8

Gly Leu Asn Pro Thr Ala Ile Phe Leu
1               5

<210> SEQ ID NO 9
<211> LENGTH: 9
<212> TYPE: PRT
<213> ORGANISM: Homo sapiens

<400> SEQUENCE: 9

Glu Leu Pro Glu Thr Leu Glu Thr Leu
1               5

<210> SEQ ID NO 10
<211> LENGTH: 9
<212> TYPE: PRT
<213> ORGANISM: Homo sapiens

<400> SEQUENCE: 10

Ala Trp Leu Val His Arg Gln Trp Phe
1               5

<210> SEQ ID NO 11
<211> LENGTH: 9
<212> TYPE: PRT
<213> ORGANISM: Homo sapiens

<400> SEQUENCE: 11

Thr Leu Tyr Ala Val Ala Thr Thr Phe
1               5

<210> SEQ ID NO 12
<211> LENGTH: 9
<212> TYPE: PRT
<213> ORGANISM: Homo sapiens

<400> SEQUENCE: 12

Ala Leu Ser Glu Leu Pro Glu Thr Leu
1               5

<210> SEQ ID NO 13
<211> LENGTH: 9
<212> TYPE: PRT
<213> ORGANISM: Homo sapiens

<400> SEQUENCE: 13

Trp Tyr Met Trp Leu Gly Ala Arg Phe
1               5

<210> SEQ ID NO 14
<211> LENGTH: 9
<212> TYPE: PRT
<213> ORGANISM: Homo sapiens
```

-continued

```
<400> SEQUENCE: 14

Ile Leu Gly Asp Thr Ala Trp Asp Phe
1               5

<210> SEQ ID NO 15
<211> LENGTH: 9
<212> TYPE: PRT
<213> ORGANISM: Homo sapiens

<400> SEQUENCE: 15

Tyr Met Pro Ser Val Ile Glu Lys Met
1               5

<210> SEQ ID NO 16
<211> LENGTH: 9
<212> TYPE: PRT
<213> ORGANISM: Homo sapiens

<400> SEQUENCE: 16

Lys Leu Met Lys Ile Thr Ala Glu Trp
1               5

<210> SEQ ID NO 17
<211> LENGTH: 9
<212> TYPE: PRT
<213> ORGANISM: Homo sapiens

<400> SEQUENCE: 17

Thr Tyr Gly Trp Asn Leu Val Arg Leu
1               5

<210> SEQ ID NO 18
<211> LENGTH: 9
<212> TYPE: PRT
<213> ORGANISM: Homo sapiens

<400> SEQUENCE: 18

Ile Gln Lys Glu Thr Leu Val Thr Phe
1               5

<210> SEQ ID NO 19
<211> LENGTH: 9
<212> TYPE: PRT
<213> ORGANISM: Homo sapiens

<400> SEQUENCE: 19

Ala Leu His Gln Val Phe Gly Ala Ile
1               5

<210> SEQ ID NO 20
<211> LENGTH: 9
<212> TYPE: PRT
<213> ORGANISM: Homo sapiens

<400> SEQUENCE: 20

Gly Phe Leu Asn Glu Asp His Trp Phe
1               5

<210> SEQ ID NO 21
<211> LENGTH: 9
<212> TYPE: PRT
<213> ORGANISM: Homo sapiens

<400> SEQUENCE: 21

Ala Leu Val Ala Phe Leu Arg Phe Leu
```

```
<210> SEQ ID NO 22
<211> LENGTH: 9
<212> TYPE: PRT
<213> ORGANISM: Homo sapiens

<400> SEQUENCE: 22

Pro Met Ser Thr Tyr Gly Trp Asn Leu
1               5

<210> SEQ ID NO 23
<211> LENGTH: 9
<212> TYPE: PRT
<213> ORGANISM: Homo sapiens

<400> SEQUENCE: 23

Ala Tyr Asn His Ala Leu Ser Glu Leu
1               5

<210> SEQ ID NO 24
<211> LENGTH: 9
<212> TYPE: PRT
<213> ORGANISM: Homo sapiens

<400> SEQUENCE: 24

Ala Tyr Thr Ile Gly Thr Thr Tyr Phe
1               5

<210> SEQ ID NO 25
<211> LENGTH: 9
<212> TYPE: PRT
<213> ORGANISM: Homo sapiens

<400> SEQUENCE: 25

Asp Trp Ile Pro Leu Ala Leu Thr Ile
1               5

<210> SEQ ID NO 26
<211> LENGTH: 9
<212> TYPE: PRT
<213> ORGANISM: Homo sapiens

<400> SEQUENCE: 26

Leu Leu Leu Thr Leu Leu Ala Thr Val
1               5

<210> SEQ ID NO 27
<211> LENGTH: 9
<212> TYPE: PRT
<213> ORGANISM: Homo sapiens

<400> SEQUENCE: 27

Ile Val Leu Glu His Gly Ser Cys Val
1               5

<210> SEQ ID NO 28
<211> LENGTH: 9
<212> TYPE: PRT
<213> ORGANISM: Homo sapiens

<400> SEQUENCE: 28

Leu Leu Phe Lys Thr Glu Asn Gly Val
1               5
```

```
<210> SEQ ID NO 29
<211> LENGTH: 9
<212> TYPE: PRT
<213> ORGANISM: Homo sapiens

<400> SEQUENCE: 29

Pro Leu Asn Glu Ala Ile Met Ala Val
1               5

<210> SEQ ID NO 30
<211> LENGTH: 9
<212> TYPE: PRT
<213> ORGANISM: Homo sapiens

<400> SEQUENCE: 30

Asn Leu Val Arg Leu Gln Ser Gly Val
1               5

<210> SEQ ID NO 31
<211> LENGTH: 9
<212> TYPE: PRT
<213> ORGANISM: Homo sapiens

<400> SEQUENCE: 31

Arg Leu Ile Thr Val Asn Pro Ile Val
1               5

<210> SEQ ID NO 32
<211> LENGTH: 9
<212> TYPE: PRT
<213> ORGANISM: Homo sapiens

<400> SEQUENCE: 32

Leu Leu Leu Val Ala His Tyr Ala Ile
1               5

<210> SEQ ID NO 33
<211> LENGTH: 9
<212> TYPE: PRT
<213> ORGANISM: Homo sapiens

<400> SEQUENCE: 33

Ile Leu Ile Arg Thr Gly Leu Leu Val
1               5

<210> SEQ ID NO 34
<211> LENGTH: 9
<212> TYPE: PRT
<213> ORGANISM: Homo sapiens

<400> SEQUENCE: 34

Ser Leu Arg Pro Gln Pro Thr Glu Leu
1               5

<210> SEQ ID NO 35
<211> LENGTH: 9
<212> TYPE: PRT
<213> ORGANISM: Homo sapiens

<400> SEQUENCE: 35

Phe Leu Ile Asp Gly Pro Glu Thr Ala
1               5

<210> SEQ ID NO 36
<211> LENGTH: 9
<212> TYPE: PRT
```

<213> ORGANISM: Homo sapiens

<400> SEQUENCE: 36

Phe Gln Pro Glu Ser Pro Ser Lys Leu
1               5

<210> SEQ ID NO 37
<211> LENGTH: 9
<212> TYPE: PRT
<213> ORGANISM: Homo sapiens

<400> SEQUENCE: 37

Ala Leu Ser Glu Leu Pro Glu Thr Leu
1               5

<210> SEQ ID NO 38
<211> LENGTH: 9
<212> TYPE: PRT
<213> ORGANISM: Homo sapiens

<400> SEQUENCE: 38

Ala Leu His Gln Val Phe Gly Ala Ile
1               5

<210> SEQ ID NO 39
<211> LENGTH: 9
<212> TYPE: PRT
<213> ORGANISM: Homo sapiens

<400> SEQUENCE: 39

Tyr Met Pro Ser Val Ile Glu Lys Met
1               5

<210> SEQ ID NO 40
<211> LENGTH: 9
<212> TYPE: PRT
<213> ORGANISM: Homo sapiens

<400> SEQUENCE: 40

Glu Leu Pro Glu Thr Leu Glu Thr Leu
1               5

<210> SEQ ID NO 41
<211> LENGTH: 9
<212> TYPE: PRT
<213> ORGANISM: Homo sapiens

<400> SEQUENCE: 41

Leu Val Ile Ser Gly Leu Phe Pro Val
1               5

<210> SEQ ID NO 42
<211> LENGTH: 9
<212> TYPE: PRT
<213> ORGANISM: Homo sapiens

<400> SEQUENCE: 42

Leu Leu Leu Val Ala His Tyr Ala Ile
1               5

<210> SEQ ID NO 43
<211> LENGTH: 9
<212> TYPE: PRT
<213> ORGANISM: Homo sapiens

<400> SEQUENCE: 43

Leu Ala Leu Leu Ala Ala Phe Lys Val
1               5

<210> SEQ ID NO 44
<211> LENGTH: 9
<212> TYPE: PRT
<213> ORGANISM: Homo sapiens

<400> SEQUENCE: 44

Val Ile Leu Ala Gly Pro Met Pro Val
1               5

<210> SEQ ID NO 45
<211> LENGTH: 9
<212> TYPE: PRT
<213> ORGANISM: Homo sapiens

<400> SEQUENCE: 45

His Val Leu Gly Arg Leu Ile Thr Val
1               5

<210> SEQ ID NO 46
<211> LENGTH: 9
<212> TYPE: PRT
<213> ORGANISM: Homo sapiens

<400> SEQUENCE: 46

Ile Val Leu Glu His Gly Ser Cys Val
1               5

<210> SEQ ID NO 47
<211> LENGTH: 9
<212> TYPE: PRT
<213> ORGANISM: Homo sapiens

<400> SEQUENCE: 47

Tyr Val Val Ile Ala Ile Leu Thr Val
1               5

<210> SEQ ID NO 48
<211> LENGTH: 9
<212> TYPE: PRT
<213> ORGANISM: Homo sapiens

<400> SEQUENCE: 48

Ser Val Ile Glu Lys Met Glu Ala Leu
1               5

<210> SEQ ID NO 49
<211> LENGTH: 9
<212> TYPE: PRT
<213> ORGANISM: Homo sapiens

<400> SEQUENCE: 49

Arg Thr Leu Arg Val Leu Asn Leu Val
1               5

<210> SEQ ID NO 50
<211> LENGTH: 9
<212> TYPE: PRT
<213> ORGANISM: Homo sapiens

<400> SEQUENCE: 50

Gln Ile Leu Glu Glu Asn Val Glu Val
1               5

<210> SEQ ID NO 51
<211> LENGTH: 3391
<212> TYPE: PRT
<213> ORGANISM: Homo sapiens

<400> SEQUENCE: 51

Met Asn Asn Gln Arg Lys Lys Ala Arg Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Thr Ala Gly Val Ile Ile Met Met Ile Pro Thr Val
            100                 105                 110

Val Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Asn Gly
    130                 135                 140

Val Asn Met Cys Thr Leu Met Ala Met Asp Leu Gly Glu Leu Cys Glu
145                 150                 155                 160

Asp Thr Ile Thr Tyr Asn Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Ala Thr Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Ala Gln Arg Ile Glu Thr Trp
225                 230                 235                 240

Val Leu Arg His Pro Gly Phe Thr Ile Met Ala Ala Ile Leu Ala Tyr
                245                 250                 255

Thr Ile Gly Thr Thr Tyr Phe Gln Arg Val Leu Ile Phe Ile Leu Leu
            260                 265                 270

Thr Ala Val Ala Pro Ser Met Thr Met Arg Cys Ile Gly Ile Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Thr Lys Thr Glu Ala Lys His Pro Ala Thr Leu
                325                 330                 335

Arg Lys Tyr Cys Ile Glu Ala Lys Leu Thr Asn Thr Thr Thr Ala Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

```
Cys Gly Leu Phe Gly Lys Gly Ile Val Thr Cys Ala Met Phe Thr
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Asn Ala Val Gly
            420                 425                 430

Asn Asp Thr Gly Lys His Gly Lys Glu Ile Lys Val Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asp Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
                500                 505                 510

Gln Lys Glu Thr Leu Val Thr Phe Lys Asn Pro His Ala Lys Lys Gln
        515                 520                 525

Asp Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
                580                 585                 590

Ala Glu Thr Gln His Gly Thr Ile Val Ile Arg Val Gln Tyr Glu Gly
            595                 600                 605

Asp Gly Ser Pro Cys Lys Ile Pro Phe Glu Ile Met Asp Leu Glu Lys
        610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Ser Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Val Ile Thr Trp Ile Gly Met Asn Ser Arg Ser
            740                 745                 750

Thr Ser Leu Ser Val Ser Leu Val Leu Val Gly Val Val Thr Leu Tyr
        755                 760                 765

Leu Gly Val Met Val Gln Ala Asp Ser Gly Cys Val Val Ser Trp Lys
770                 775                 780

Asn Lys Glu Leu Lys Cys Gly Ser Gly Ile Phe Ile Thr Asp Asn Val
                785                 790                 795                 800

His Thr Trp Thr Glu Gln Tyr Lys Phe Gln Pro Glu Ser Pro Ser Lys
```

-continued

```
                805                 810                 815
Leu Ala Ser Ala Ile Gln Lys Ala His Glu Glu Gly Ile Cys Gly Ile
            820                 825                 830

Arg Ser Val Thr Arg Leu Glu Asn Leu Met Trp Lys Gln Ile Thr Pro
            835                 840                 845

Glu Leu Asn His Ile Leu Ser Glu Asn Glu Val Lys Leu Thr Ile Met
850                 855                 860

Thr Gly Asp Ile Lys Gly Ile Met Gln Ala Gly Lys Arg Ser Leu Arg
865                 870                 875                 880

Pro Gln Pro Thr Glu Leu Lys Tyr Ser Trp Lys Ala Trp Gly Lys Ala
            885                 890                 895

Lys Met Leu Ser Thr Glu Leu His Asn His Thr Phe Leu Ile Asp Gly
            900                 905                 910

Pro Glu Thr Ala Glu Cys Pro Asn Thr Asn Arg Ala Trp Asn Ser Leu
            915                 920                 925

Glu Val Glu Asp Tyr Gly Phe Gly Val Phe Thr Thr Asn Ile Trp Leu
            930                 935                 940

Lys Leu Lys Glu Arg Gln Asp Val Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
            980                 985                 990

Ile Glu Val Lys Ser Cys His Trp Pro Lys Ser His Thr Leu Trp Ser
            995                 1000                1005

Asn Gly Val Leu Glu Ser Glu Met Ile Ile Pro Lys Asn Phe Ala
        1010                1015                1020

Gly Pro Val Ser Gln His Asn Tyr Arg Pro Gly Tyr His Thr Gln
        1025                1030                1035

Thr Ala Gly Pro Trp His Leu Gly Lys Leu Glu Met Asp Phe Asp
        1040                1045                1050

Phe Cys Glu Gly Thr Thr Val Val Val Thr Glu Asp Cys Gly Asn
        1055                1060                1065

Arg Gly Pro Ser Leu Arg Thr Thr Thr Ala Ser Gly Lys Leu Ile
        1070                1075                1080

Thr Glu Trp Cys Cys Arg Ser Cys Thr Leu Pro Pro Leu Arg Tyr
        1085                1090                1095

Arg Gly Glu Asp Gly Cys Trp Tyr Gly Met Glu Ile Arg Pro Leu
        1100                1105                1110

Lys Glu Lys Glu Glu Asn Leu Val Asn Ser Leu Val Thr Ala Gly
        1115                1120                1125

His Gly Gln Ile Asp Asn Phe Ser Leu Gly Val Trp Gly Met Ala
        1130                1135                1140

Leu Phe Leu Glu Glu Met Leu Arg Thr Arg Val Gly Thr Lys His
        1145                1150                1155

Ala Ile Leu Leu Val Ala Val Ser Phe Val Thr Leu Ile Thr Gly
        1160                1165                1170

Asn Met Ser Phe Arg Asp Leu Gly Arg Val Met Val Met Val Gly
        1175                1180                1185

Ala Thr Met Thr Asp Asp Ile Gly Met Gly Val Thr Tyr Leu Ala
        1190                1195                1200

Leu Leu Ala Ala Phe Lys Val Arg Pro Thr Phe Ala Ala Gly Leu
        1205                1210                1215
```

```
Leu Leu Arg Lys Leu Thr Ser Lys Glu Leu Met Met Thr Thr Ile
1220                1225                1230

Gly Ile Val Leu Leu Ser Gln Ser Thr Ile Pro Glu Thr Ile Leu
1235                1240                1245

Glu Leu Thr Asp Ala Leu Ala Leu Gly Met Met Val Leu Lys Ile
1250                1255                1260

Val Arg Asn Met Glu Lys Tyr Gln Leu Ala Val Thr Ile Met Ala
1265                1270                1275

Ile Leu Cys Val Pro Asn Ala Val Ile Leu Gln Asn Ala Trp Lys
1280                1285                1290

Val Ser Cys Thr Ile Leu Ala Val Val Ser Val Ser Pro Leu Leu
1295                1300                1305

Leu Thr Ser Ser Gln Gln Lys Ala Asp Trp Ile Pro Leu Ala Leu
1310                1315                1320

Thr Ile Lys Gly Leu Asn Pro Thr Ala Ile Phe Leu Thr Thr Leu
1325                1330                1335

Ser Arg Thr Ser Lys Lys Arg Ser Trp Pro Leu Asn Glu Ala Ile
1340                1345                1350

Met Ala Val Gly Met Val Ser Ile Leu Ala Ser Ser Leu Leu Lys
1355                1360                1365

Asn Asp Ile Pro Met Thr Gly Pro Leu Val Ala Gly Gly Leu Leu
1370                1375                1380

Thr Val Cys Tyr Val Leu Thr Gly Arg Ser Ala Asp Leu Glu Leu
1385                1390                1395

Glu Arg Ala Ala Asp Val Arg Trp Glu Glu Gln Ala Glu Ile Ser
1400                1405                1410

Gly Ser Ser Pro Ile Leu Ser Ile Thr Ile Ser Glu Asp Gly Ser
1415                1420                1425

Met Ser Ile Lys Asn Glu Glu Glu Gln Thr Leu Thr Ile Leu
1430                1435                1440

Ile Arg Thr Gly Leu Leu Val Ile Ser Gly Leu Phe Pro Val Ser
1445                1450                1455

Ile Pro Ile Thr Ala Ala Ala Trp Tyr Leu Trp Glu Val Lys Lys
1460                1465                1470

Gln Arg Ala Gly Val Leu Trp Asp Val Pro Ser Pro Pro Pro Val
1475                1480                1485

Gly Lys Ala Glu Leu Glu Asp Gly Ala Tyr Arg Ile Lys Gln Lys
1490                1495                1500

Gly Ile Leu Gly Tyr Ser Gln Ile Gly Ala Gly Val Tyr Lys Glu
1505                1510                1515

Gly Thr Phe His Thr Met Trp His Val Thr Arg Gly Ala Val Leu
1520                1525                1530

Met His Lys Gly Lys Arg Ile Glu Pro Ser Trp Ala Asp Val Lys
1535                1540                1545

Lys Asp Leu Ile Ser Tyr Gly Gly Gly Trp Lys Leu Glu Gly Glu
1550                1555                1560

Trp Lys Glu Gly Glu Glu Val Gln Val Leu Ala Leu Glu Pro Gly
1565                1570                1575

Lys Asn Pro Arg Ala Val Gln Thr Lys Pro Gly Leu Phe Lys Thr
1580                1585                1590

Asn Thr Gly Thr Ile Gly Ala Val Ser Leu Asp Phe Ser Pro Gly
1595                1600                1605

Thr Ser Gly Ser Pro Ile Val Asp Lys Lys Gly Lys Val Val Gly
1610                1615                1620
```

```
Leu Tyr Gly Asn Gly Val Val Thr Arg Ser Gly Thr Tyr Val Ser
    1625            1630                1635

Ala Ile Ala Gln Thr Glu Lys Ser Ile Glu Asp Asn Pro Glu Ile
    1640            1645                1650

Glu Asp Asp Ile Phe Arg Lys Lys Arg Leu Thr Ile Met Asp Leu
    1655            1660                1665

His Pro Gly Ala Gly Lys Thr Lys Arg Tyr Leu Pro Ala Ile Val
    1670            1675                1680

Arg Glu Ala Ile Lys Arg Gly Leu Arg Thr Leu Ile Leu Ala Pro
    1685            1690                1695

Thr Arg Val Val Ala Ala Glu Met Glu Glu Ala Leu Arg Gly Leu
    1700            1705                1710

Pro Ile Arg Tyr Gln Thr Pro Ala Ile Arg Ala Glu His Thr Gly
    1715            1720                1725

Arg Glu Ile Val Asp Leu Met Cys His Ala Thr Phe Thr Met Arg
    1730            1735                1740

Leu Leu Ser Pro Ile Arg Val Pro Asn Tyr Asn Leu Ile Ile Met
    1745            1750                1755

Asp Glu Ala His Phe Thr Asp Pro Ala Ser Ile Ala Ala Arg Gly
    1760            1765                1770

Tyr Ile Ser Thr Arg Val Glu Met Gly Glu Ala Ala Gly Ile Phe
    1775            1780                1785

Met Thr Ala Thr Pro Pro Gly Ser Arg Asp Pro Phe Pro Gln Ser
    1790            1795                1800

Asn Ala Pro Ile Met Asp Glu Glu Arg Glu Ile Pro Glu Arg Ser
    1805            1810                1815

Trp Asn Ser Gly His Glu Trp Val Thr Asp Phe Lys Gly Lys Thr
    1820            1825                1830

Val Trp Phe Val Pro Ser Ile Lys Ala Gly Asn Asp Ile Ala Ala
    1835            1840                1845

Cys Leu Arg Lys Asn Gly Lys Lys Val Ile Gln Leu Ser Arg Lys
    1850            1855                1860

Thr Phe Asp Ser Glu Tyr Val Lys Thr Arg Thr Asn Asp Trp Asp
    1865            1870                1875

Phe Val Val Thr Thr Asp Ile Ser Glu Met Gly Ala Asn Phe Lys
    1880            1885                1890

Ala Glu Arg Val Ile Asp Pro Arg Arg Cys Met Lys Pro Val Ile
    1895            1900                1905

Leu Thr Asp Gly Glu Glu Arg Val Ile Leu Ala Gly Pro Met Pro
    1910            1915                1920

Val Thr His Ser Ser Ala Ala Gln Arg Arg Gly Arg Val Gly Arg
    1925            1930                1935

Asn Pro Lys Asn Glu Asn Asp Gln Tyr Ile Tyr Met Gly Glu Pro
    1940            1945                1950

Leu Glu Asn Asp Glu Asp Cys Ala His Trp Lys Glu Ala Lys Met
    1955            1960                1965

Leu Leu Asp Asn Ile Asn Thr Pro Glu Gly Ile Ile Pro Ser Met
    1970            1975                1980

Phe Glu Pro Glu Arg Glu Lys Val Asp Ala Ile Asp Gly Glu Tyr
    1985            1990                1995

Arg Leu Arg Gly Glu Ala Arg Lys Thr Phe Val Asp Leu Met Arg
    2000            2005                2010

Arg Gly Asp Leu Pro Val Trp Leu Ala Tyr Arg Val Ala Ala Glu
```

-continued

```
                2015                2020                2025

Gly Ile Asn Tyr Ala Asp Arg Arg Trp Cys Phe Asp Gly Val Lys
    2030                2035                2040

Asn Asn Gln Ile Leu Glu Glu Asn Val Glu Val Glu Ile Trp Thr
    2045                2050                2055

Lys Glu Gly Glu Arg Lys Lys Leu Lys Pro Arg Trp Leu Asp Ala
    2060                2065                2070

Arg Ile Tyr Ser Asp Pro Leu Ala Leu Lys Glu Phe Lys Glu Phe
    2075                2080                2085

Ala Ala Gly Arg Lys Ser Leu Thr Leu Asn Leu Ile Thr Glu Met
    2090                2095                2100

Gly Arg Leu Pro Thr Phe Met Thr Gln Lys Ala Arg Asn Ala Leu
    2105                2110                2115

Asp Asn Leu Ala Val Leu His Thr Ala Glu Ala Gly Gly Arg Ala
    2120                2125                2130

Tyr Asn His Ala Leu Ser Glu Leu Pro Glu Thr Leu Glu Thr Leu
    2135                2140                2145

Leu Leu Leu Thr Leu Leu Ala Thr Val Thr Gly Gly Ile Phe Leu
    2150                2155                2160

Phe Leu Met Ser Gly Lys Gly Ile Gly Lys Met Thr Leu Gly Met
    2165                2170                2175

Cys Cys Ile Ile Thr Ala Ser Val Leu Leu Trp Tyr Ala Gln Ile
    2180                2185                2190

Gln Pro His Trp Ile Ala Ala Ser Ile Ile Leu Glu Phe Phe Leu
    2195                2200                2205

Ile Val Leu Leu Ile Pro Glu Pro Glu Lys Gln Arg Thr Pro Gln
    2210                2215                2220

Asp Asn Gln Leu Thr Tyr Val Val Ile Ala Ile Leu Thr Val Val
    2225                2230                2235

Ala Ala Thr Met Ala Asn Glu Met Gly Phe Leu Glu Lys Thr Lys
    2240                2245                2250

Lys Asp Phe Gly Leu Gly Gly Ile Ala Thr Gln Gln Pro Glu Ser
    2255                2260                2265

Asn Ile Leu Asp Ile Asp Leu Arg Pro Ala Ser Ala Trp Thr Leu
    2270                2275                2280

Tyr Ala Val Ala Thr Thr Phe Ile Thr Pro Met Leu Arg His Ser
    2285                2290                2295

Ile Glu Asn Ser Ser Val Asn Val Ser Leu Thr Ala Ile Ala Asn
    2300                2305                2310

Gln Ala Thr Val Leu Met Gly Leu Gly Lys Gly Trp Pro Leu Ser
    2315                2320                2325

Lys Met Asp Ile Gly Val Pro Leu Leu Ala Ile Gly Cys Tyr Ser
    2330                2335                2340

Gln Val Asn Pro Ile Thr Leu Thr Ala Ala Leu Leu Leu Leu Val
    2345                2350                2355

Ala His Tyr Ala Ile Ile Gly Pro Gly Leu Gln Ala Lys Ala Thr
    2360                2365                2370

Arg Glu Ala Gln Lys Arg Ala Ala Ala Gly Ile Met Lys Asn Pro
    2375                2380                2385

Thr Val Asp Gly Ile Thr Val Ile Asp Leu Asp Pro Ile Pro Tyr
    2390                2395                2400

Asp Pro Lys Phe Glu Lys Gln Leu Gly Gln Val Met Leu Leu Val
    2405                2410                2415
```

-continued

Leu Cys Val Thr Gln Val Leu Met Met Arg Thr Thr Trp Ala Leu
2420                2425                2430

Cys Glu Ala Leu Thr Leu Ala Thr Gly Pro Ile Ser Thr Leu Trp
2435                2440                2445

Glu Gly Asn Pro Gly Arg Phe Trp Asn Thr Thr Ile Ala Val Ser
2450                2455                2460

Met Ala Asn Ile Phe Arg Gly Ser Tyr Leu Ala Gly Ala Gly Leu
2465                2470                2475

Leu Phe Ser Ile Met Lys Asn Thr Ala Asn Thr Arg Arg Gly Thr
2480                2485                2490

Gly Asn Thr Gly Glu Thr Leu Gly Glu Lys Trp Lys Asn Arg Leu
2495                2500                2505

Asn Ala Leu Gly Lys Ser Glu Phe Gln Ile Tyr Lys Lys Ser Gly
2510                2515                2520

Ile Gln Glu Val Asp Arg Thr Leu Ala Lys Glu Gly Ile Lys Arg
2525                2530                2535

Gly Glu Thr Asp His His Ala Val Ser Arg Gly Ser Ala Lys Leu
2540                2545                2550

Arg Trp Phe Val Glu Arg Asn Leu Val Thr Pro Glu Gly Lys Val
2555                2560                2565

Met Asp Leu Gly Cys Gly Arg Gly Gly Trp Ser Tyr Tyr Cys Gly
2570                2575                2580

Gly Leu Lys Asn Val Lys Glu Val Lys Gly Leu Thr Lys Gly Gly
2585                2590                2595

Pro Gly His Glu Glu Pro Ile Pro Met Ser Thr Tyr Gly Trp Asn
2600                2605                2610

Leu Val Arg Leu Gln Ser Gly Val Asp Val Phe Phe Thr Pro Pro
2615                2620                2625

Glu Lys Cys Asp Thr Leu Leu Cys Asp Ile Gly Glu Ser Ser Pro
2630                2635                2640

Asn Pro Thr Val Glu Ala Gly Arg Thr Leu Arg Val Leu Asn Leu
2645                2650                2655

Val Glu Asn Trp Leu Asn Asn Asn Thr Gln Phe Cys Ile Lys Val
2660                2665                2670

Leu Asn Pro Tyr Met Pro Ser Val Ile Glu Lys Met Glu Ala Leu
2675                2680                2685

Gln Arg Lys Tyr Gly Gly Ala Leu Val Arg Asn Pro Leu Ser Arg
2690                2695                2700

Asn Ser Thr His Glu Met Tyr Trp Val Ser Asn Ala Ser Gly Asn
2705                2710                2715

Ile Val Ser Ser Val Asn Met Ile Ser Arg Met Leu Ile Asn Arg
2720                2725                2730

Phe Thr Met Arg His Lys Lys Ala Thr Tyr Glu Pro Asp Val Asp
2735                2740                2745

Leu Gly Ser Gly Thr Arg Asn Ile Gly Ile Glu Ser Glu Ile Pro
2750                2755                2760

Asn Leu Asp Ile Ile Gly Lys Arg Ile Glu Lys Ile Lys Gln Glu
2765                2770                2775

His Glu Thr Ser Trp His Tyr Asp Gln Asp His Pro Tyr Lys Thr
2780                2785                2790

Trp Ala Tyr His Gly Ser Tyr Glu Thr Lys Gln Thr Gly Ser Ala
2795                2800                2805

Ser Ser Met Val Asn Gly Val Val Arg Leu Leu Thr Lys Pro Trp
2810                2815                2820

-continued

```
Asp Val Ile Pro Met Val Thr Gln Met Ala Met Thr Asp Thr Thr
2825                2830                2835

Pro Phe Gly Gln Gln Arg Val Phe Lys Glu Lys Val Asp Thr Arg
2840                2845                2850

Thr Gln Glu Pro Lys Glu Gly Thr Lys Lys Leu Met Lys Ile Thr
2855                2860                2865

Ala Glu Trp Leu Trp Lys Glu Leu Gly Lys Lys Lys Thr Pro Arg
2870                2875                2880

Met Cys Thr Arg Glu Glu Phe Thr Arg Lys Val Arg Ser Asn Ala
2885                2890                2895

Ala Leu Gly Ala Ile Phe Thr Asp Glu Asn Lys Trp Lys Ser Ala
2900                2905                2910

Arg Glu Ala Val Glu Asp Ser Gly Phe Trp Glu Leu Val Asp Lys
2915                2920                2925

Glu Arg Asn Leu His Leu Glu Gly Lys Cys Glu Thr Cys Val Tyr
2930                2935                2940

Asn Met Met Gly Lys Arg Glu Lys Lys Leu Gly Glu Phe Gly Lys
2945                2950                2955

Ala Lys Gly Ser Arg Ala Ile Trp Tyr Met Trp Leu Gly Ala Arg
2960                2965                2970

Phe Leu Glu Phe Glu Ala Leu Gly Phe Leu Asn Glu Asp His Trp
2975                2980                2985

Phe Ser Arg Glu Asn Ser Leu Ser Gly Val Glu Arg Glu Gly Leu
2990                2995                3000

His Lys Leu Gly Tyr Ile Leu Arg Asp Val Ser Lys Lys Glu Gly
3005                3010                3015

Gly Ala Met Tyr Ala Asp Asp Thr Ala Gly Trp Asp Thr Arg Ile
3020                3025                3030

Thr Leu Glu Asp Leu Lys Asn Glu Glu Met Val Thr Asn His Met
3035                3040                3045

Glu Gly Glu His Lys Lys Leu Ala Glu Ala Ile Phe Lys Leu Thr
3050                3055                3060

Tyr Gln Asn Lys Val Val Arg Val Gln Arg Pro Thr Pro Arg Gly
3065                3070                3075

Thr Val Met Asp Ile Ile Ser Arg Arg Asp Gln Arg Gly Ser Gly
3080                3085                3090

Gln Val Val Thr Tyr Gly Leu Asn Thr Phe Thr Asn Met Glu Ala
3095                3100                3105

Gln Leu Ile Arg Gln Met Glu Gly Glu Gly Val Phe Lys Ser Ile
3110                3115                3120

Gln Gln Leu Thr Ala Thr Glu Glu Ile Ala Val Lys Asn Trp Leu
3125                3130                3135

Ala Arg Val Gly Arg Glu Arg Leu Ser Arg Met Ala Ile Ser Gly
3140                3145                3150

Asp Asp Cys Val Val Lys Pro Leu Asp Asp Arg Phe Ala Ser Ala
3155                3160                3165

Leu Thr Ala Leu Asn Asp Met Gly Lys Val Arg Lys Asp Ile Gln
3170                3175                3180

Gln Trp Glu Pro Ser Arg Gly Trp Asn Asp Trp Thr Gln Val Pro
3185                3190                3195

Phe Cys Ser His His Phe His Glu Leu Ile Met Lys Asp Gly Arg
3200                3205                3210

Val Leu Val Val Pro Cys Arg Asn Gln Asp Glu Leu Ile Gly Arg
```

-continued

```
            3215                3220                3225
Ala Arg Ile Ser Gln Gly Ala Gly Trp Ser Leu Arg Glu Thr Ala
    3230                3235                3240
Cys Leu Gly Lys Ser Tyr Ala Gln Met Trp Ser Leu Met Tyr Phe
    3245                3250                3255
His Arg Arg Asp Leu Arg Leu Ala Ala Asn Ala Ile Cys Ser Ala
    3260                3265                3270
Val Pro Ser His Trp Val Pro Thr Ser Arg Thr Thr Trp Ser Ile
    3275                3280                3285
His Ala Thr His Glu Trp Met Thr Thr Glu Asp Met Leu Thr Val
    3290                3295                3300
Trp Asn Arg Val Trp Ile Gln Glu Asn Pro Trp Ile Glu Asp Lys
    3305                3310                3315
Thr Pro Val Glu Ser Trp Glu Glu Ile Pro Tyr Leu Gly Lys Arg
    3320                3325                3330
Glu Asp Gln Trp Cys Gly Ser Leu Ile Gly Leu Thr Ser Arg Ala
    3335                3340                3345
Thr Trp Ala Lys Asn Ile Gln Thr Ala Ile Asn Gln Val Arg Ser
    3350                3355                3360
Leu Ile Gly Asn Glu Glu Tyr Thr Asp Tyr Met Pro Ser Met Lys
    3365                3370                3375
Arg Phe Arg Arg Glu Glu Glu Ala Gly Val Leu Trp
    3380                3385                3390
```

HLA-BINDING PEPTIDE, PRECURSOR THEREOF, DNA FRAGMENT AND RECOMBINANT VECTOR ENCODING THE SAME

TECHNICAL FIELD

The present invention relates to an HLA-binding peptide, precursor thereof, DNA fragment and recombinant vector encoding the same.

BACKGROUND ART

Human leukocyte antigen (HLA) genes are located on the short arm of chromosome 6. HLAs are classified into class I molecules (HLA-A type, B type and C type) and class II molecules (HLA-DP type, DQ type and DR type). In specific immune response, when cytotoxic T cells (CTL) recognize cell surface antigens such as tumor cells, transplanted cells and virus infected cells, it is essential to recognize the cells with class I molecules. Class I molecules are present on the membrane surface of almost all cells.

When cells are infected with a virus such as dengue virus, innate immunity is triggered to induce a reaction to eliminate the virus. After that comes specific immune response to induce a reaction to eliminate the viruses.

In specific immune response, the viruses in body fluids are eliminated by neutralizing antibodies. The viruses inside the cell are eliminated by cytotoxic T cells (CTL). Thus, CTLs specifically recognize the viral antigen (CTL epitope) composed of 8 to 11 amino acids presented by the HLA class I molecules on the infected cell surface, and eliminate the viruses by inducing damage to the infected cells. Therefore, it is important to identify such virus-specific CTL epitopes in order to produce preventive and therapeutic vaccines for the viruses.

One of such techniques is described in Patent Document 1, which discloses that an oligopeptide consisting of a certain amino acid sequence is capable of binging to HLA.

Patent Document 1: Japanese Patent Laid-Open No. 8-151396

DISCLOSURE OF THE INVENTION

Problems to be Solved by the Invention

However, there were several points to improve with the related art described in the above document, wherein the points will be described below.

First, it is not known whether the HLA-binding peptide described in the above document effectively binds to an HLA molecule. The binding to HLA could be further improved.

Second, it is described that the HLA-binding peptide described in the above document is capable of binding to HLA-DQ4. However, it is not known whether it can bind to an HLA-A2 type molecule (the product of HLA-A*0201 gene, HLA-A*0206 gene and the like) that is common in Westerners and to an HLA-A24 type molecule (the product of HLA-A*2402 gene and the like) that is common in the Japanese people.

The present invention has been made based on the above circumstances. It provides an HLA-binding peptide being excellent in binding affinity to specific types of HLA molecules.

Means for Solving the Problems

According to the present invention, there is provided an HLA-binding peptide capable of binding to an HLA-A type molecule, wherein the peptide includes one or more amino acid sequences selected from the group consisting of SEQ ID NOs: 1 to 50, and is composed of 8 or more and 11 or less amino acid residues.

Advantage of the Invention

According to the present invention, there is provided an HLA-binding peptide being excellent in binding affinity to an HLA-A type molecule because the peptide includes a specific amino acid sequence.

BRIEF DESCRIPTION OF THE DRAWING

FIG. 1 is a schematic view that describes the active learning experiment design used in Examples.

BEST MODE FOR CARRYING OUT THE INVENTION

Hereinafter, exemplary embodiments will be described using drawings. In all of the drawings, the same symbols are used for the same components, and descriptions will be arbitrarily abbreviated.

Exemplary Embodiment 1

In the present exemplary embodiment, peptides predicted by the hypotheses obtained by the active learning experiment method (Japanese Patent Laid-Open No. 11-316754), including an amino acid sequence whose binding affinity to an HLA molecule is defined as 3 or higher in −log Kd value, and which is composed of 8 or more and 11 or less amino acid residues were defined as candidate HLA-binding peptides. As a result of a binding experiment, the peptides were confirmed to be actually HLA-binding peptides.

As a result, a number of HLA-binding peptides were efficiently obtained, wherein the peptides were excellent binders to HLA-A type molecules because they included the amino acid sequence whose binding affinity to an HLA molecule was defined as 3 or higher in −log Kd value.

More specifically, the HLA-binding peptides in the present exemplary embodiment is an HLA-binding peptide capable of binding to an HLA-A type molecule, including one or more amino acid sequences selected from the group consisting of SEQ ID NOs: 1 to 50 to be described below, and being composed of 8 or more and 11 or less amino acid residues.

Of the human HLA-A types, approximately 50% of the Japanese people have HLA-A24 type. Many Westerners such as Germans have HLA-A2 type.

In addition, all of the sequences are composed of 9 amino acid residues included in the certain genome protein of dengue virus, which causes dengue fever.

SEQ ID NOs: 1 to 25 are shown in Table 1 below.

TABLE 1

| HLA-A24 type binding peptide | | | | |
|---|---|---|---|---|
| SEQ ID NO | Top 30 predicted scores | Predicted score | Sequence name | Binding experiment data |
| 1 | WYAQIQPHW | 6.4821 | 2189 | 8.64465 |
| 2 | AFSGVSWTM | 6.2931 | 727 | 8.19335 |
| 3 | ILIGVVITW | 6.2629 | 737 | |

TABLE 1-continued

HLA-A24 type binding peptide

| SEQ ID NO | Top 30 predicted scores | Predicted score | Sequence name | Binding experiment data |
|---|---|---|---|---|
| 4 | MMIPTVVAF | 6.2445 | 107 | 7.80808 |
| 5 | PFPQSNAPI | 6.1924 | 1799 | 8.22128 |
| 6 | LHKLGYILR | 6.1857 | 3003 | |
| 7 | HWPKSHTLW | 6.1631 | 999 | 8.65937 |
| 8 | GLNPTAIFL | 6.0286 | 1327 | 6.39195 |
| 9 | ELPETLETL | 6.0259 | 2140 | 7.00975 |
| 10 | AWLVHRQWF | 5.9475 | 485 | 8.38884 |
| 11 | TLYAVATTF | 5.9382 | 2282 | 7.58458 |
| 12 | ALSELPETL | 5.919 | 2137 | 5.505 |
| 13 | WYMWLGARF | 5.9025 | 2966 | 7.62792 |
| 14 | ILGDTAWDF | 5.8777 | 694 | 7.38687 |
| 15 | YMPSVIEKM | 5.831 | 2677 | 7.16873 |
| 16 | KLMKITAEW | 5.8074 | 2863 | 7.20712 |
| 17 | TYGWNLVRL | 5.7904 | 2609 | 7.41537 |
| 18 | IQKETLVTF | 5.7333 | 512 | 7.2378 |
| 19 | ALHQVFGAI | 5.7111 | 715 | 6.05453 |
| 20 | GFLNEDHWF | 5.6281 | 2981 | 6.7592 |
| 21 | ALVAFLRFL | 5.5909 | 49 | 5.68122 |
| 22 | PMSTYGWNL | 5.5847 | 2606 | 7.62376 |
| 23 | AYNHALSEL | 5.5579 | 2133 | 7.67924 |
| 24 | AYTIGTTYF | 5.5429 | 255 | 7.33162 |
| 25 | DWIPLALTI | 5.5177 | 1317 | 8.00347 |

The sequences represented by SEQ ID NOs: 1 to 25 are composed of 9 amino acid residues included in the representative strain, AY776328, of dengue virus type 2 (serotype type 2). In addition, the sequences represented by SEQ ID NOs: 1 to 25 are predicted to have high binding affinity to an HLA-A24 molecule (the product of HLA-A*2402 gene) by using the above method. SEQ ID NOs: 1 to 25 are listed in the descending order of binding affinity. More specifically, SEQ ID NO: 1 is the sequence predicted to have the highest binding affinity. Values given as predicted binding scores and experimentally obtained binding affinity data with an HLA-A24 molecule of each sequence are shown in −log Kd values.

SEQ ID NOs: 26 to 40 are shown in Table 2 below.

TABLE 2

HLA-A2 type binding peptide

| SEQ ID NO | Top 30 predicted scores | Predicted score | Sequence name | Binding experiment data |
|---|---|---|---|---|
| 26 | LLLTLLATV | 6.3869 | 2149 | |
| 27 | IVLEHGSCV | 5.8802 | 303 | 5.73645 |

TABLE 2-continued

HLA-A2 type binding peptide

| SEQ ID NO | Top 30 predicted scores | Predicted score | Sequence name | Binding experiment data |
|---|---|---|---|---|
| 28 | LLFKTENGV | 5.7903 | 137 | 7.4752 |
| 29 | PLNEAIMAV | 5.7853 | 1348 | 6.49478 |
| 30 | NLVRLQSGV | 5.5324 | 2613 | 4.69767 |
| 31 | RLITVNPIV | 5.528 | 630 | 5.64013 |
| 32 | LLLVAHYAI | 5.4766 | 2355 | 6.0465 |
| 33 | ILIRTGLLV | 5.4029 | 1442 | 6.52543 |
| 34 | SLRPQPTEL | 5.3835 | 878 | 5.0502 |
| 35 | FLIDGPETA | 5.3509 | 908 | 6.05413 |
| 36 | FQPESPSKL | 5.34 | 809 | 6.31273 |
| 37 | ALSELPETL | 5.3249 | 2137 | 6.04526 |
| 38 | ALHQVFGAI | 5.096 | 715 | 6.76833 |
| 39 | YMPSVIEKM | 5.087 | 2677 | 6.5755 |
| 40 | ELPETLETL | 5.0571 | 2140 | 6.32394 |

The sequences represented by SEQ ID NOs: 26 to 40 are composed of 9 amino acid residues included in the representative strain, AY776328, of dengue virus type 2. In addition, the sequences represented by SEQ ID NOs: 26 to 40 are predicted to have high binding affinity to an HLA-A2 molecule (the product of HLA-A*0201 gene) by using the above method. SEQ ID NOs: 26 to 40 are listed in the descending order of binding affinity. More specifically, SEQ ID NO: 26 is the sequence predicted to have the highest binding affinity. Values given as predicted binding scores and experimentally obtained binding affinity data with an HLA-A2 molecule of each sequence are shown in −log Kd values.

SEQ ID NOs: 41 to 50 are shown in Table 3 below.

TABLE 3

HLA-A2 type binding peptide

| SEQ ID NO | Top 10 predicted scores | Predicted score | Sequence name | Binding experiment data |
|---|---|---|---|---|
| 41 | LVISGLFPV | 6.5075 | 1449 | 6.61148 |
| 42 | LLLVAHYAI | 6.4483 | 2355 | 6.23631 |
| 43 | LALLAAFKV | 6.2137 | 1202 | 6.46715 |
| 44 | VILAGPMPV | 6.0883 | 1916 | 6.17305 |
| 45 | HVLGRLITV | 6.0414 | 626 | 6.25386 |
| 46 | IVLEHGSCV | 6.039 | 303 | 6.02114 |
| 47 | YVVIAILTV | 5.7103 | 2229 | 5.86017 |
| 48 | SVIEKMEAL | 5.7097 | 2680 | 6.37418 |
| 49 | RTLRVLNLV | 5.6558 | 2651 | 5.96642 |
| 50 | QILEENVEV | 5.6349 | 2046 | 5.60512 |

The sequences represented by SEQ ID NOs: 41 to 50 are composed of 9 amino acid residues included in the representative strain, AY776328, of dengue virus type 2. In addition, the sequences represented by SEQ ID NOs: 41 to 50 are predicted to have high binding affinity to an HLA-A2 molecule (the product of HLA-A*0206 gene) by using the above method. SEQ ID NOs: 41 to 50 are listed in the descending order of binding affinity. More specifically, SEQ ID NO: 41 is the sequence predicted to have the highest binding affinity. Values given as predicted binding scores and experimentally obtained binding affinity data with an HLA-A2 molecule of each sequence are shown in −log Kd values.

As will be described in detail hereinafter, there is clearly a relationship between the predicted scores and binding experiment data in Tables 1 to 3. More specifically, the peptides predicted to have high binding affinity to an HLA-A molecule by using the above method were experimentally confirmed to have high binding affinity to an HLA-A molecule with some degree of inaccuracy.

Previously, the method for searching HLA-binding peptides by using the experiment design method has not been used. Therefore, there have been only few known HLA-binding peptides, wherein the peptides were experimentally confirmed to have binding affinity to an HLA molecule. Thus, when peptides composed of 9 amino acid residues that were randomly synthesized by the conventional method were subjected to binding experiment with an HLA-molecule, there was stochastically only 1 in approximately 100 molecules, whose binding affinity exhibited 6 or higher in −log Kd value.

In the present exemplary embodiment, the method for searching HLA-binding peptides by using the experiment design method was adopted. As a result, as many as 50 HLA-binding peptide sequences were successfully identified as described above. Moreover, some of the obtained HLA-binding peptides were experimentally tested for their binding affinity to HLA. It was confirmed that all of the tested sequences had the same or higher level of binding affinity to HLA in comparison to the prediction.

Moreover, of the sequences, an HLA-binding peptide including one or more amino acid sequences selected from the group consisting of SEQ ID NOs: 1, 2, 4, 5, 7, 8, 9, 10, 11, 12, 13, 14, 15, 16, 17, 18, 19, 20, 21, 22, 23, 24, 25, 27, 28, 29, 30, 31, 32, 33, 34, 35, 36, 37, 38, 39, 40, 41, 42, 43, 44, 45, 46, 47, 48, 49 and 50 was experimentally confirmed to have binding affinity to a human HLA-A type molecule. Therefore, the peptides are certainly regarded as HLA-binding peptides being excellent in binding affinity to a human HLA-A type molecule.

With regards to the HLA-binding peptides in the present exemplary embodiment, the binding affinity to an HLA molecule is defined as 3 or higher, particularly preferably 5 or higher, and more preferably 5.4 or higher in −log Kd value.

In the field of biochemistry, binding affinity defined as approximately 3 in −log Kd value is known to be the binding threshold for a peptide to MHCs such as HLAs. Therefore, if the binding affinity to an HLA molecule is defined as 3 or higher in −log Kd value, the peptide can be regarded as an HLA-binding peptide.

Moreover, in case of an HLA-A24 molecule, if the binding affinity to an HLA-A24 molecule is defined as 5 or higher in −log Kd value, a peptide being excellent in binding affinity to an HLA molecule can be obtained. The peptide can be preferably used to develop an effective therapeutic drug, preventive drug and the like for immune disease and the like.

In addition, if the binding affinity to an HLA-A24 molecule is defined as 5.4 or higher in −log Kd value, a peptide being particularly excellent in binding affinity to an HLA molecule can be obtained. The peptide can be preferably used to develop a further effective therapeutic drug, preventive drug and the like for immune disease and the like.

Furthermore, the HLA-binding peptide in the present exemplary embodiment may be composed of 8 or more and 11 or less amino acid residues.

If a peptide is composed of 8 or more and 11 or less amino acid residues as described above, the peptide is excellent in binding affinity to an HLA molecule. Moreover, cytotoxic T cells (CTL) specifically recognize the viral antigen (CTL epitope) composed of 8 to 11 amino acids presented by the HLA class I molecules on the surface of virus-infected cells and the like, and eliminate the viruses by inducing damage to the infected cells. Therefore, it is important to produce such virus-specific CTL epitopes composed of 8 to 11 amino acids in order to produce preventive and therapeutic vaccines for the viruses.

For example, the above HLA-binding peptide may be a peptide solely composed of amino acid residues, but it is not particularly limited thereto. For example, it may be an HLA-binding peptide precursor, wherein the precursor is modified with a sugar chain, fatty acid residue and the like according to need as long as the modification does not interfere with the effective activity of the present invention. The precursor is converted into an HLA-binding peptide by digestion with a digestive enzyme and the like in vivo in mammals such as human digestive organs. The above HLA-binding peptide exerts a similar effective activity to that of the binding peptide.

In addition, the above HLA-binding peptide may be a peptide capable of binding to a human HLA-A24 molecule.

Moreover, the above HLA-binding peptide may be a peptide capable of binding to a human HLA-A2 molecule.

According to the constitutions, a peptide that binds to an HLA-A24 molecule, which is common in Asians including the Japanese people, is obtained. Therefore, the peptide can be used to develop an effective therapeutic drug, preventive drug and the like particularly suited for Asians including the Japanese people.

Moreover, according to the constitutions, a peptide that binds to an HLA-A2 molecule, which is common in Westerners in addition to the Japanese people, is obtained. Therefore, the peptide can be used to develop an effective therapeutic drug, preventive drug and the like particularly suited for Westerners in addition to the Japanese people.

In addition, the amino acid sequence included in the above HLA-binding peptide may be an amino acid sequence derived from a certain genome protein of dengue virus, but it is not particularly limited thereto. For example, it may be an amino acid sequence derived from HIV protein, amino acid sequence derived from cedar pollen protein and the like. Moreover, it may include an amino acid sequence derived from a protein that has other pathogenicity or allergenicity.

For example, if it includes an amino acid sequence derived from dengue virus, an HLA-binding peptide that can be used to prevent and treat the disease caused by dengue virus is obtained.

Exemplary Embodiment 2

According to the present exemplary embodiment, there is provided an HLA-binding peptide capable of binding to an HLA-A type molecule, wherein the peptide comprises an amino acid sequence in which one or two amino acid residues have been deleted, substituted or added in the amino acid sequence contained in the above HLA-binding peptide, and the peptide is composed of 8 or more and 11 or less amino acid residues.

As will be described in detail below, the constitution including an amino acid sequence in which one or several amino acid residues have been deleted, substituted or added in the specific amino acid sequence that has binding affinity to an HLA-A type molecule exerts a similar effect to that of the HLA-binding peptide in the above exemplary embodiment 1.

Moreover, of the amino acid sequences being excellent in binding affinity to an HLA-A molecule represented by SEQ ID NOs: 1 to 50, an amino acid sequence in which one or two amino acid residues have been substituted, deleted or added is predicted to exert similarly excellent binding affinity to HLA.

From another perspective, of the amino acid sequences being excellent in binding affinity to an HLA-A molecule predicted by the above method, an amino acid sequence in which one or several amino acid residues have been substituted, deleted or added is predicted to exert similarly excellent binding affinity to HLA. Moreover, it is preferable that both the amino acid residues involved in substitution have similar properties such as hydrophobic amino acid residues.

In addition, the HLA-binding peptides described in exemplary embodiments 1 and 2 can be manufactured by a method known to a person skilled in the art. For example, the peptides can be artificially synthesized by the solid phase method or the liquid phase method. Moreover, the HLA-binding peptides can be manufactured by expressing DNA fragments or recombinant vectors encoding the HLA-binding peptides. The obtained HLA-binding peptides can be identified by a method known to a person skilled in the art. For example, they can be identified by using the Edman degradation method, mass spectrometry and the like.

Exemplary Embodiment 3

According to the present exemplary embodiment, there is provided a DNA fragment including a DNA sequence that encodes the above HLA-binding peptide. The DNA fragment in the present exemplary embodiment can express the above HLA-binding peptide because it includes the specific DNA sequence.

In addition, in order to express the above HLA-binding peptide by using the DNA fragment in the present exemplary embodiment, the DNA fragment may be introduced into the cell for expression, or may be expressed by using a commercially available artificial protein expression kit.

Moreover, the above DNA fragment may be introduced into the human cell for persistent expression. Therefore, the HLA-binding peptide is allowed to be present in the cell more persistently when the DNA fragment encoding the HLA-binding peptide is introduced into the cell than it is when the HLA-binding peptide itself is introduced into the cell. When the HLA-binding peptide is used as vaccine, it is advantageous to have the ability of persistent expression in order to enhance vaccine effectiveness.

Furthermore, the DNA fragment in the present exemplary embodiment can be manufactured by a method known to a person skilled in the art. For example, it may be artificially synthesized by a commercially available DNA synthesizer and the like. Alternatively, it may be cut out from the dengue virus genome with a restriction enzyme and the like. It can be also obtained by amplifying the dengue virus genome by the PCR method with primers. The obtained DNA fragments can be identified by a method known to a person skilled in the art. For example, they can be identified by a commercially available DNA sequencer and the like.

Exemplary Embodiment 4

According to the present exemplary embodiment, there is provided a recombinant vector including a DNA sequence that encodes the above HLA-binding peptide. The recombinant vector in the present exemplary embodiment can express the above HLA-binding peptide because it includes the specific DNA sequence.

In addition, in order to express the above HLA-binding peptide by using the recombinant vector in the present exemplary embodiment, the recombinant vector may be introduced into the cell for expression, or may be expressed by using a commercially available artificial protein expression kit.

Moreover, the above recombinant vector may be introduced into the human cell for persistent expression. Therefore, the HLA-binding peptide is allowed to be present in the cell more persistently when the recombinant vector encoding the HLA-binding peptide is introduced into the cell than it is when the HLA-binding peptide itself is introduced into the cell. When the HLA-binding peptide is used as vaccine, it is advantageous to have the ability of persistent expression in order to enhance vaccine effectiveness.

In addition, when the above recombinant vector is used, the expression level of the HLA-binding peptide can be accurately controlled by using an arbitrary sequence in the regulatory region for transcription and expression such as the promoter region upstream of the DNA sequence that encodes the above HLA-binding peptide. The number of copies of the recombinant vector in the cell can be accurately controlled by using an arbitrary sequence in the regulatory region for replication such as the origin region of the recombinant vector.

Moreover, the above recombinant vector may include an arbitrary sequence in addition to the DNA sequence encoding the above HLA-binding peptide. For example, it may include a marker gene sequence such as a drug resistance gene.

In addition, the recombinant vector in the present exemplary embodiment can be manufactured by a method known to a person skilled in the art. For example, it may be obtained by cleaving the multi-cloning site of a commercially available vector such as pBR322 and pUC19 at an arbitrary restriction site, inserting the above DNA fragment to the site, and ligating to the vector. The obtained recombinant vector can be identified by a method known to a person skilled in the art. For example, it can be identified by performing agarose gel electrophoresis to confirm whether the lengths of the cleaved DNA fragments with an arbitrary restriction enzyme match to the cleavage map of the commercially available vector such as pBR322 and pUC19, and confirming the presence of the above DNA sequence in the DNA sequence cut out from the multi-cloning site by using DNA sequencer and the like.

The above exemplary embodiments, however, are merely for exemplification of the present invention only, and various other constitutions can be adopted other than the ones described above.

For example, in the above exemplary embodiments, an HLA-binding peptide including an amino acid sequence derived from the certain genome protein of dengue virus was used. However, it may be an HLA-binding peptide including an amino acid sequence derived from another protein of dengue virus. In such cases, the peptide can be used to treat various immune diseases involving the protein from which it was derived.

Moreover, it may be an HLA-binding peptide for pathogens other than dengue virus, such as HIV virus. It may also be an HLA-binding peptide including an amino acid sequence derived from allergens such as cedar pollen, or proteins in cancer cells and the like.

In addition, when such peptide are used, if the peptides include an amino acid sequence predicted to be excellent in binding affinity to an HLA molecule by using the above method, it is considered that the peptides will be experimentally confirmed to have similarly excellent binding affinity to HLA. Therefore, the HLA-binding peptides can be preferably used for treating or preventing especially infectious diseases (dengue fever, influenza, SARS, HIV, HCV and the like) as well as cancer immunotherapy (Wilms Tumor 1, MAGE and the like), allergic disorders (pollen allergy, rheumatism, atopy, asthma and the like), autoimmune disease and the like.

EXAMPLES

Although examples will be described in detail hereinafter, it is to be understood that the invention is not restricted to these particular examples.

More specifically, the procedures for prediction, experiment and evaluation used in the present example were based on the active learning experiment design. Overall, the following steps were repeated. FIG. 1 is a schematic view that describes the active learning experiment design used herein.

(1) Run the hypostasis learning algorithm to be described hereinafter once. In other words, derive multiple hypotheses from the accumulated data by random re-sampling, and select the point that has the largest variance in the predicted values for the randomly expressed candidate query points (peptides) as the query point to be experimented.

(2) Synthesize the peptide at the selected query point by the synthesis and purification methods to be described hereinafter. Measure the actual binding affinity by the experiment to be described hereinafter, and add the affinity value to the accumulated data.

In the present example, a supervised learning algorithm based on the Hidden Markov Model was used as the hypostasis learning algorithm. Starting from the initial data for 223 peptides, a range of 20 to 30 kinds of peptides were predicted and selected per experiment. By repeating the above procedures 4 times, a total of 341 data was obtained.

More specifically, in the active learning method in the present example, we designed and synthesized a range of 20 to 30 kinds of peptides composed of an amino acid sequence that was aligned by 9 amino acids selected from the 20 amino acids in one experiment. Subsequently, we measured the strength of their binding to an HLA molecule (binding affinity). As a result, we obtained the binding affinity (Kd value) as the experimental results. The peptides with high binding affinity were regarded as the candidates for an HLA-binding peptide applicable for vaccine material.

Subsequently, we input the obtained results into the learning system equipped with learning machines that utilized the Hidden Markov Model as a mathematical algorithm in order to set the rules. We allowed each of the learning machines to take samples of different results, and set the rules. Moreover, the expressed rules were of different constitutions for each of the learning machines. In addition, the obtained rules and experimental data were loaded as the accumulated data on an as-needed basis.

Subsequently, according to the rules, we selected the next experimental candidates from the $20^9=500$ billion peptide sequences or more, and repeated the above processes. In doing this, we applied different rules for the experimental candidates, and performed the experiment only for the candidates over which the predictions for the experimental results were divided. We could improve the final prediction accuracy because the candidates over which the predictions for the experimental results were divided were subjected to the next experiment as described above.

As described above, we performed selective sampling to select the samples that were predicted differently by multiple learning machines as the experimental candidates. As a result, we obtained information efficiently and gained the highly accurate hypotheses (rules). By repeating the above processes 4 times, excellent results in the example to be described hereinafter were obtained. Moreover, repeating the above processes 7 times or more, further excellent results can be obtained.

By performing the active learning method, we could reduce the number of binding experiments required for the peptides composed of 9 amino acid residues. In theory, all of the 500 billion candidate HLA-binding peptides or more had to be examined. In the active learning method, we prepared the rules from the experiments, and repeated the experiments for a few dozen of candidate sequences predicted by applying the rules. As a result, we could significantly reduce the time and cost required for the initial screening by cutting the number of experiments.

In addition, the frequency of encountering the HLA-binding peptides reached a range of 70 to 80% by using the prediction which uses the rules obtained by the active learning method described above. In contrast, the frequency of encountering the HLA-binding peptides by using other known technologies such as the Anchor method is merely in the range of 30%.

<Synthesis and Purification of Peptides>

Peptides were manually synthesized by using Fmoc amino acids and the Merrifield solid phase method. After deprotection, the peptides were purified by reversed phase HPLC using C18 columns to achieve the purity of 95% or more. To identify the peptides and confirm their purity, MALDI-TOF mass analysis was performed (Voyager DE RP, PerSeptive). To quantify the peptides, Micro BCA assay (Thermo Scientific Pierce) was performed by using BSA as a standard protein.

<Binding Experiment of the Peptides to an HLA-A2402 Molecule>

The peptides' binding affinity to an HLA-A24 molecule (the product of HLA-A*2402 gene) was measured by using C1R-A24 cells that express the HLA-A*2402 gene (produced by and provided with permission of Professor Masafumi Takiguchi, Kumamoto University).

First, the C1R-A24 cells were exposed to the acidic condition of pH 3.3 for 30 seconds to dissociate and remove the endogenous peptides that were originally bound to an HLA-A2402 molecule and the light chain β 2 m that was commonly assembled with HLA class I molecules. After neutralization, the C1R-A24 cells were added with purified β 2 m, and the mixture was added to a peptide serial dilution. Then, the mixture was incubated on ice for 4 hours. The 3-molecule assembly (MHC-pep) composed of the HLA-A2402 molecule, peptide and β 2 m, which had been reassembled during the incubation, was stained by using the fluorescent labeled monoclonal antibody, 17A12 that recognizes the assembly.

Subsequently, the number of MHC-pep per C1R-A24 cell (which is proportional to the fluorescent intensity of the above fluorescent antibody) was quantitatively measured by using a fluorescent cell analysis machine, FACScan (Becton, Dickinson and Company). The binding dissociation constant, Kd value, between the HLA-A24 molecule and peptide was calculated from the average fluorescent intensity per cell by using the method published in the research article (Udaka et al., Immunogenetics, 51, 816-828, 2000).

<Binding Experiment of the Peptides to an HLA-A0201 Molecule>

The peptides' binding affinity to an HLA-A2 molecule (the product of HLA-A*0201 gene) was measured by using the cell line JY that expresses the HLA-A*0201 gene (obtained from ATCC (American Type Culture Collection)).

First, the JY cells were exposed to the acidic condition of pH 3.8 for 30 seconds to dissociate and remove the endogenous peptides and light chain β 2 m that had been non-covalently bound to an HLA-A0201 molecule. After neutralization, a reassemble experiment was performed.

The above JY cells and purified β 2 m were added to a serial dilution of the peptide whose binding affinity was to be measured. Then, the mixture was incubated on ice for 4 hours. The HLA-A0201 molecule that had been reassembled up to this point was stained by using the assembly-specific fluorescent labeled monoclonal antibody, BB7.2.

Subsequently, the amount of fluorescence per cell was measured by using a flow cytometer. The dissociation constant, Kd value, was calculated by using the method published in the research article (Udaka et al., Immunogenetics, 51, 816-828, 2000).

<Binding Experiment of the Peptides to an HLA-A0206 Molecule>

The peptides' binding affinity to an HLA-A2 molecule (the product of HLA-A*0206 gene) was measured by using RA2.6 cells (a newly prepared cell line at Kochi University) that express the HLA-A*0206 gene, which were created by expressing cDNA of the HLA-A*0206 gene in RAMS cells, the mouse TAP peptide transporter deficient cells.

First, the RA2.6 cells were cultured overnight at 26° C. to accumulate HLA-A0206 molecules that were unbound to peptides on the cell surface. A peptide serial dilution was added thereto for binding at room temperature for 30 minutes.

Subsequently, the mixture was cultured for 3.5 hours at 37° C. to denature the empty HLA-A0206 molecules that were unbound to peptides. As a result, the HLA-A0206 molecules lost their steric structure.

Either the fluorescent labeled monoclonal antibody 17A10 or 17A12, which specifically recognizes a peptide-bound HLA-A0206 molecule, was added thereto. The mixture was incubated on ice for 20 minutes, and the cells were stained.

Subsequently, the amount of fluorescence per cell was measured by using a flow cytometer. The dissociation constant, Kd value, was calculated by using the method published in the research article (Udaka et al., Immunogenetics, 51, 816-828, 2000).

<Evaluation Results>

As a result, the prediction results and experimental results shown in the above Tables 1 to 3 were obtained.

The sequences represented by SEQ ID NOs: 1 to 25 in Table 1 are the sequences composed of 9 amino acid residues included in the representative strain, AY776328, of dengue virus type 2 that is registered in GENBANK. Moreover, the sequences represented by SEQ ID NOs: 1 to 25 are the sequences which were predicted to have high binding affinity to an HLA-A24 molecule (the product of HLA-A*2402 gene) using the hypotheses obtained by the experiment design method described in the exemplary embodiment 1. In addition, SEQ ID NOs: 1 to 25 are listed in the descending order of binding affinity. More specifically, SEQ ID NO: 1 is the sequence predicted to have the highest binding affinity. Moreover, the entire amino acid sequence of the representative strain, AY776328, of dengue virus type 2

(MNNQRKKARNTPFNMLKRERNRVSTVQQLTKRFSLGMLQGRGPLKLFMA
LVAFLRFLTIPPTAGILKRWGTIKKSKAINVLRGFRKEIGRMLNILNRRR
RTAGVIIMMIPTVVAFHLTTRNGEPHMIVSRQEKGKSLLFKTENGVNMCT
LMAMDLGELCEDTITYNCPLLRQNEPEDIDCWCNSTSTWVTYGTCTATGE
HRREKRSVALVPHVGMGLETRTETWMSSEGAWKHAQRIETWVLRHPGFTI
MAAILAYTIGTTYFQRVLIFILLTAVAPSMTMRCIGISNRDFVEGVSGGS
WVDIVLEHGSCVTTMAKNKPTLDFELTKTEAKHPATLRKYCIEAKLTNTT
TASRCPTQGEPSLNEEQDKRFVCKHSMVDRGWGNGCGLFGKGGIVTCAMF
TCKKNMEGKVVQPENLEYTIVITPHSGEENAVGNDTGKHGKEIKVTPQSS
ITEAELTGYGTVTMECSPRTGLDFNEMVLLQMEDKAWLVHRQWFLDLPLP
WLPGADTQGSNWIQKETLVTFKNPHAKKQDVVVLGSQEGAMHTALTGATE
IQMSSGNLLFTGHLKCRLRMDKLQLKGMSYSMCTGKFKVVKEIAETQHGT
IVIRVQYEGDGSPCKIPFEIMDLEKRHVLGRLITVNPIVTEKDSPVNIEA
EPPFGDSYIIIGVEPGQLKLSWFKKGSSIGQMFETTMRGAKRMAILGDTA
WDFGSLGGVFTSIGKALHQVFGAIYGAAFSGVSWTMKILIGVVITWIGMN
SRSTSLSVSLVLVGVVTLYLGVMVQADSGCVVSWKNKELKCGSGIFITDN
VHTWTEQYKFQPESPSKLASAIQKAHEEGICGIRSVTRLENLMWKQITPE
LNHILSENEVKLTIMTGDIKGIMQAGKRSLRPQPTELKYSWKAWGKAKML
STELHNHTFLIDGPETAECPNTNRAWNSLEVEDYGFGVFTTNIWLKLKER
QDVFCDSKLMSAAIKDNRAVHADMGYWIESALNDTWKIEKASFIEVKSCH
WPKSHTLWSNGVLESEMIIPKNFAGPVSQHNYRPGYHTQTAGPWHLGKLE
MDFDFCEGTTVVVTEDCGNRGPSLRTTTASGKLITEWCCRSCTLPPLRYR
GEDGCWYGMEIRPLKEKEENLVNSLVTAGHGQIDNFSLGVWGMALFLEEM
LRTRVGTKHAILLVAVSFVTLITGNMSFRDLGRVMVMVGATMTDDIGMGV
TYLALLAAFKVRPTFAAGLLLRKLTSKELMMTTIGIVLLSQSTIPETILE
LTDALALGMMVLKIVRNMEKYQLAVTIMAILCVPNAVILQNAWKVSCTIL
AVVSVSPLLLTSSQQKADWIPLALTIKGLNPTAIFLTTLSRTSKKRSWPL
NEAIMAVGMVSILASSLLKNDIPMTGPLVAGGLLTVCYVLTGRSADLELE
RAADVRWEEQAEISGSSPILSITISEDGSMSIKNEEEEQTLTILIRTGLL
VISGLFPVSIPITAAAWYLWEVKKQRAGVLWDVPSPPPVGKAELEDGAYR
IKQKGILGYSQIGAGVYKEGTFHTMWHVTRGAVLMHKGKRIEPSWADVKK
DLISYGGGWKLEGEWKEGEEVQVLALEPGKNPRAVQTKPGLFKTNTGTIG
AVSLDFSPGTSGSPIVDKKGKVVGLYGNGVVTRSGTYVSAIAQTEKSIED
NPEIEDDIFRKKRLTIMDLHPGAGKTKRYLPAIVREAIKRGLRTLILAPT
RVVAAEMEEALRGLPIRYQTPAIRAEHTGREIVDLMCHATFTMRLLSPIR
VPNYNLIIMDEAHFTDPASIAARGYISTRVEMGEAAGIFMTATPPGSRDP
FPQSNAPIMDEEREIPERSWNSGHEWVTDFKGKTVWFVPSIKAGNDIAAC
LRKNGKKVIQLSRKTFDSEYVKTRTNDWDFVVTTDISEMGANFKAERVID
PRRCMKPVILTDGEERVILAGPMPVTHSSAAQRRGRVGRNPKNENDQYIY
MGEPLENDEDCAHWKEAKMLLDNINTPEGIIPSMFEPEREKVDAIDGEYR
LRGEARKTFVDLMRRGDLPVWLAYRVAAEGINYADRRWCFDGVKNNQILE

-continued

ENVEVEIWTKEGERKKLKPRWLDARIYSDPLALKEFKEFAAGRKSLTLNL

ITEMGRLPTFMTQKARNALDNLAVLHTAEAGGRAYNHALSELPETLETLL

LLTLLATVTGGIFLFLMSGKGIGKMTLGMCCIITASVLLWYAQIQPHWIA

ASIILEFFLIVLLIPEPEKQRTPQDNQLTYVVIAILTVVAATMANEMGFL

EKTKKDFGLGGIATQQPESNILDIDLRPASAWTLYAVATTFITPMLRHSI

ENSSVNVSLTAIANQATVLMGLGKGWPLSKMDIGVPLLAIGCYSQVNPIT

LTAALLLLVAHYAIIGPGLQAKATREAQKRAAAGIMKNPTVDGITVIDLD

PIPYDPKFEKQLGQVMLLVLCWQVLMMRTTWALCEALTLATGPISTLWEG

NPGRFWNTTIAVSMANIFRGSYLAGAGLLFSIMKNTANTRRGTGNTGETL

GEKWKNRLNALGKSEFQIYKKSGIQEVDRTLAKEGIKRGETDHHAVSRGS

AKLRWFVERNLVTPEGKVMDLGCGRGGWSYYCGGLKNVKEVKGLTKGGPG

HEEPIPMSTYGWNLVRLQSGVDVFFTPPEKCDTLLCDIGESSPNPTVEAG

RTLRVLNLVENWLNNNTQFCIKVLNPYMPSVIEKMEALQRKYGGALVRNP

LSRNSTHEMYWVSNASGNIVSSVNMISRMLINRFTMRHKKATYEPDVDLG

SGTRNIGIESEIPNLDIIGKRIEKIKQEHETSWHYDQDHPYKTWAYHGSY

ETKQTGSASSMVNGVVRLLTKPWDVIPMVTQMAMTDTTPFGQQRVFKEKV

DTRTQEPKEGTKKLMKITAEWLWKELGKKKTPRMCTREEFTRKVRSNAAL

GAIFTDENKWKSAREAVEDSGFWELVDKERNLHLEGKCETCVYNMMGKRE

KKLGEFGKAKGSRAIWYMWLGARFLEFEALGFLNEDHWFSRENSLSGVER

EGLHKLGYILRDVSKKEGGAMYADDTAGWDTRITLEDLKNEEMVTNHMEG

EHKKLAEAIFKLTYQNKVVRVQRPTPRGTVMDIISRRDQRGSGQVVTYGL

NTFTNMEAQLIRQMEGEGVFKSIQQLTATEEIAVKNWLARVGRERLSRMA

ISGDDCVVKPLDDRFASALTALNDMGKVRKDIQQWEPSRGWNDWTQVPFC

SHHFHELIMKDGRVLVVPCRNQDELIGRARISQGAGWSLRETACLGKSYA

QMWSLMYFHRRDLRLAANAICSAVPSHWVPTSRTTWSIHATHEWMTTEDM

LTVWNRVWIQENPWIEDKTPVESWEEIPYLGKREDQWCGSLIGLTSRATW

AKNIQTAINQVRSLIGNEEYTDYMPSMKRFRREEEEAGVLW)

is shown in SEQ ID NO: 51

In addition, the sequences represented by SEQ ID NOs: 26 to 40 in Table 2 are the sequences composed of 9 amino acid residues included in the representative strain, AY776328, of the above dengue virus type 2. Moreover, the sequences represented by SEQ ID NOs: 26 to 40 are the sequences which were predicted to have high binding affinity to an HLA-A2 molecule (the product of HLA-A*0201 gene) using the hypotheses obtained by the experiment design method described in the exemplary embodiment 1. In addition, SEQ ID NOs: 26 to 40 are listed in the descending order of binding affinity. More specifically, SEQ ID NO: 26 is the sequence predicted to have the highest binding affinity.

Furthermore, the sequences represented by SEQ ID NOs: 41 to 50 in Table 3 are the sequences composed of 9 amino acid residues included in the representative strain, AY776328, of the above dengue virus type 2. Moreover, the sequences represented by SEQ ID NOs: 41 to 50 are the sequences which were predicted to have high binding affinity to an HLA-A2 molecule (the product of HLA-A*0206 gene) using the hypotheses obtained by the experiment design method described in the exemplary embodiment 1. In addition, SEQ ID NOs: 41 to 50 are listed in the descending order of binding affinity. More specifically, SEQ ID NO: 41 is the sequence predicted to have the highest binding affinity.

In addition, Tables 1 to 3 show the amino acid sequences corresponding to the top predicted score results by using the above prediction program, predicted scores, and the corresponding binding experiment data with regards to the 9 amino acid residues included in the representative strain, AY776328, of the above dengue virus type 2. Moreover, all of the binding experiments were performed by artificially synthesizing the 9 amino acid peptides by the above synthesis method.

All of the above peptide sequences in which one or two amino acid residues are substituted respectively are predicted to exert similarly excellent binding affinity to an HLA-A molecule. Thus, of the amino acid sequences being excellent in binding affinity to an HLA-A molecule represented by SEQ ID NOs: 1 to 50, an amino acid sequence in which one or several amino acid residues have been substituted, deleted or added is predicted to exert similarly excellent binding affinity to HLA.

From another perspective, of the amino acid sequences being excellent in binding affinity to an HLA-A molecule, wherein the sequences were predicted by the hypotheses obtained by the experiment design method described in the exemplary embodiment 1, an amino acid sequence in which one or several amino acid residues have been substituted, deleted or added is regarded to exert similarly excellent binding affinity to HLA. Moreover, it is preferable that the amino acid residues to be substituted respectively have similar properties such as hydrophobic amino acid residues.

One of the present inventors, Udaka, et al. has already reported that the peptide sequences in which one or two amino acid residues have been substituted respectively show similarly excellent binding affinity to an antigen presenting molecule.

1. "Decrypting the structure of MHC-I restricted CTL epitopes with complex peptide libraries." Keiko Udaka, Karl-Heinz Wiesmuller, Stefan Kienle, Gunter Jung and Peter Walden. J. Exp. Med. 181, 2097-2108. (1995)
2. "Tolerance to amino acid varidations in peptides binding to the MHC class I protein H-2Kb." Keiko Udaka, Karl-Heinz Wiesmuller, Stefan Kienle, Gunter Jung and Peter Walden. J. Biol. Chem. 270, 24130-24134. (1995)
3. "Self MHC-restricted peptides recognized by all alloreactive T lymphocyte clone." Keiko Udaka, Karl-Heinz Wiesmuller, Stefan Kienle, Gunter Jung and Peter Walden. J. Immunol. 157, 670-678. (1996)

Therefore, the above peptide sequences in which one or two amino acid residues have been substituted respectively are predicted to exert similarly excellent binding affinity to an HLA-A molecule. Thus, of the amino acid sequences being excellent in binding affinity to an HLA-A molecule represented by SEQ ID NOs: 1 to 50, an amino acid sequence in which one or several amino acids have been substituted, deleted or added is predicted to exert similarly excellent binding affinity to HLA.

From another perspective, of the amino acid sequences being excellent in binding affinity to an HLA-A molecule, wherein the sequences were predicted by the hypotheses obtained by the experiment design method described in the exemplary embodiment 1, an amino acid sequence in which one or several amino acid residues have been substituted, deleted or added is regarded to exert similarly excellent binding affinity to HLA. Moreover, it is preferable that the amino acid residues to be substituted respectively have similar properties such as hydrophobic amino acid residues.

The present invention has been described based on the examples. However, the examples are merely for exemplification only. It is to be understood by those skilled in the art that various modifications can be made and are within the scope of this invention.

This application claims priority based on Japanese Patent Application No: 2006-279232 filed on Oct. 12, 2006 and Japanese Patent Application No: 2007-189047 filed on Jul. 20, 2007. The disclosure of the applications is incorporated herein in its entirety.

The invention claimed is:

1. An HLA-binding peptide capable of binding to an HLA-A type molecule, characterized in that the peptide comprises the amino acid sequence of SEQ ID NO: 15, and wherein said HLA-binding peptide is composed of 11 or less amino acid residues.

2. An HLA-binding peptide capable of binding to an HLA-A type molecule, characterized in that the peptide comprises the amino acid sequence of SEQ ID NO: 15 in which one amino acid residue has been deleted, substituted or added and wherein said HLA-binding peptide is composed of 8 or more and 11 or less amino acid residues.

3. The HLA-binding peptide according to claim 1, characterized in that the HLA-binding peptide binds to an HLA-A24 molecule.

4. The HLA-binding peptide according to claim 3, wherein the HLA-A24 molecule is an HLA-A2402 molecule.

5. The HLA-binding peptide according to claim 1, characterized in that the HLA-binding peptide binds to an HLA-A2 molecule.

6. The HLA-binding peptide according to claim 5, wherein the HLA-A2 molecule is an HLA-A0201 molecule.

7. The HLA-binding peptide according to claim 5, wherein the HLA-A2 molecule is an HLA-A0206 molecule.

\* \* \* \* \*